United States Patent
Trupiano et al.

(12) 
(10) Patent No.: US 11,007,044 B2
(45) Date of Patent: May 18, 2021

(54) SELF ADHERING IMPLANTABLE MESH PROSTHESIS WITH REDUCED INSERTION PROFILE

(71) Applicant: C.R. Bard, Inc., Murray Hill, NJ (US)

(72) Inventors: Anthony Trupiano, Lakeville, MA (US); Stephen N. Eldridge, Exeter, RI (US); Donald A. Coelho, Jr., Bellingham, MA (US); Kevin J. Ranucci, Warwick, RI (US); Roger E. Darois, North Kingstown, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 163 days.

(21) Appl. No.: 16/191,511

(22) Filed: Nov. 15, 2018

(65) Prior Publication Data

US 2019/0076229 A1 Mar. 14, 2019

Related U.S. Application Data

(63) Continuation of application No. 13/460,938, filed on May 1, 2012, now Pat. No. 10,159,552.

(51) Int. Cl.
*A61F 2/00* (2006.01)

(52) U.S. Cl.
CPC .......... *A61F 2/0063* (2013.01); *A61F 2/0077* (2013.01); *A61F 2002/0068* (2013.01); *A61F 2230/0091* (2013.01)

(58) Field of Classification Search
CPC .................. A61F 2/0063; A61F 2/0077; A61F 2002/0068; A61F 2002/0072;
(Continued)

(56) References Cited

U.S. PATENT DOCUMENTS

| | | | | |
|---|---|---|---|---|
| 4,769,038 | A | * | 9/1988 | Bendavid ............... A61B 17/04 606/151 |
| 5,147,374 | A | * | 9/1992 | Fernandez ............ A61F 2/0063 606/151 |

(Continued)

FOREIGN PATENT DOCUMENTS

| | | |
|---|---|---|
| FR | 2 863 502 A1 | 6/2005 |
| FR | 2 920 671 A1 | 3/2009 |

(Continued)

OTHER PUBLICATIONS

Extended European Search Report for European Application No. 13784580.6, dated Oct. 8 2015, 6 pages.

(Continued)

*Primary Examiner* — Tuan V Nguyen
*Assistant Examiner* — Charles M Wei
(74) *Attorney, Agent, or Firm* — Wolf, Greenfield & Sacks, P.C.

(57) ABSTRACT

The present invention is an implantable adhesive mesh prosthesis for reinforcing and/or repairing a defect in tissue that is easy to roll into a small diameter cylinder or other low-profile shape for passing through a trocar, incision, or other surgical instrument. More specifically, the adhesive may be applied to the mesh material in a pattern that leaves a significant portion of the surface area of the mesh material free of adhesive. In one embodiment, the adhesive is applied only near the outer perimeter of the mesh product. In another embodiment, the adhesive is applied in spots over all or a portion the surface of the mesh product. In yet another embodiment, the adhesive is applied in parallel lines on the surface of the mesh product and the mesh may be rolled up around an axis parallel to the lines of adhesive.

7 Claims, 5 Drawing Sheets

(58) Field of Classification Search
CPC ...... A61F 2230/0091; A61F 2230/0093; A61F 2/00–2002/018; A61B 17/12168–12177
See application file for complete search history.

(56) References Cited

U.S. PATENT DOCUMENTS

| | | | | |
|---|---|---|---|---|
| 5,304,187 | A * | 4/1994 | Green | A61F 2/0063 604/13 |
| 5,309,896 | A * | 5/1994 | Moll | A61B 17/00234 128/898 |
| 5,356,432 | A * | 10/1994 | Rutkow | A61B 17/0057 600/37 |
| 5,743,917 | A * | 4/1998 | Saxon | A61B 17/0057 128/898 |
| 5,954,767 | A | 9/1999 | Pajotin et al. | |
| 6,660,901 | B2 | 12/2003 | Church | |
| 7,044,982 | B2 * | 5/2006 | Milbocker | A61P 1/04 623/23.72 |
| 7,943,811 | B2 * | 5/2011 | Da Silva Macedo, Jr. | A61F 13/0203 602/42 |
| 8,221,451 | B2 * | 7/2012 | Mavani | A61B 17/0057 606/213 |
| 2003/0065357 | A1 * | 4/2003 | Dedo | A61B 17/1322 606/203 |
| 2003/0181988 | A1 * | 9/2003 | Rousseau | A61F 2/0063 623/23.72 |
| 2003/0187495 | A1 * | 10/2003 | Cully | A61B 17/12109 623/1.15 |
| 2004/0117032 | A1 * | 6/2004 | Roth | A61B 17/320016 623/23.72 |
| 2005/0129733 | A1 | 6/2005 | Milbocker et al. | |
| 2005/0283246 | A1 * | 12/2005 | Cauthen, III | A61B 17/0057 623/17.16 |
| 2005/0288691 | A1 | 12/2005 | Leiboff | |
| 2006/0064175 | A1 * | 3/2006 | Pelissier | A61F 2/0063 623/23.72 |
| 2007/0129736 | A1 | 6/2007 | Solecki | |
| 2008/0129733 | A1 | 6/2008 | Andersson | |
| 2008/0206305 | A1 | 8/2008 | Herweck et al. | |
| 2009/0041824 | A1 * | 2/2009 | Zugates | A61K 9/0024 424/423 |
| 2010/0069930 | A1 | 3/2010 | Roslin et al. | |
| 2010/0305589 | A1 * | 12/2010 | Solecki | A61L 24/0042 606/151 |
| 2011/0313406 | A1 | 12/2011 | Fortier et al. | |
| 2013/0296897 | A1 | 11/2013 | Trupiano et al. | |

FOREIGN PATENT DOCUMENTS

| | | | |
|---|---|---|---|
| WO | WO 2008/082444 A2 | 7/2008 | |
| WO | WO-2008082444 A2 * | 7/2008 | ......... A61F 13/0253 |

OTHER PUBLICATIONS

Office Action for European Application No. 13784580.6, dated Feb. 8, 2017, 5 pages.
[No Author Listed] A true three-dimensional, anatomically formed mesh for use in laparoscopic inguinal hernia repair. Davol: A Bard Company. 2007, 2 pages.

* cited by examiner

SELF ADHERING IMPLANTABLE MESH PROSTHESIS WITH REDUCED INSERTION PROFILE

RELATED APPLICATIONS

This Application is a Continuation of U.S. application Ser. No. 13/460,938, filed May 1, 2012, entitled "SELF ADHERING IMPLANTABLE MESH PROSTHESIS WITH REDUCED INSERTION PROFILE".

FIELD OF INVENTION

The present invention relates to self adhering implantable mesh prostheses.

BACKGROUND OF THE INVENTION

Various prosthetic mesh materials have been proposed to reinforce the abdominal wall and to close abdominal wall defects in animals (including humans). It has been known to repair hernias and other tissue defects and tears by implanting a sheet of surgical mesh fabric prosthesis that is stitched to the surrounding tissue. Commonly, a flat or three dimensional sheet that is appropriately sized and shaped for the particular repair is introduced to the surgical site through an incision in the skin and/or through a trocar or other tubular surgical device. A three dimensional prosthesis might be formed, for instance, by manufacturing a flat sheet of mesh and then heat forming it into a predetermined shape in a mold or on a mandrill.

Hence, the mesh fabric typically is folded into a cylindrical shape with a relatively narrow diameter in order to pass through the incision or trocar. In one technique using a trocar, for example, the surgeon grasps the mesh with a long-nosed surgical grasper and pushes the grasper and mesh through the trocar into the body leading with the distal end of the grasper and with the mesh trailing behind it and folding up around the long jaws of the grasper. The mesh will inherently fold upon itself to pass through the trocar and then can expand back toward its natural shape once it has passed completely through the trocar. After insertion into the animal's body cavity, the surgeon may need to manipulate the mesh with the grasper or another surgical tool in order to spread it out fully into the proper shape and navigate it to the desired position.

In another technique, the mesh is specifically rolled like a cigar into a small-diameter tube and grasped by a surgical grasper with the leading end of the grasper grasping what will be the leading longitudinal end of the tube of mesh material and the rest of the mesh tube disposed between the long jaws of the grasper tool (or possibly disposed with one jaw of the grasper tool within the rolled up prosthesis and the other jaw outside of the mesh tube). The mesh is passed through the trocar, other surgical instrument, or incision and expanded just as described above.

After the prosthesis is introduced into the body and properly positioned, it is fixed to the tissue over the repair site. Traditionally, the mesh is fixed by suturing. However, more recently, mesh prostheses have been developed with a layer of adhesive disposed on a surface thereof so that the mesh prostheses may be adhered to the tissue, rather than stitched. The adhesive typically is pressure activated (i.e., it will stick upon being pressed firmly against the tissue). In addition, the adhesive may be activated (i.e., become sticky) when it is exposed to moisture. Hence, the mesh is kept dry prior to introduction into the patient's body so that it may be rolled up into a narrow tube (or other low profile shape) without sticking to itself. However, once the prosthesis is introduced into the body, it is likely to become wet, and thus sticky, quickly. Thus, once it is in the body, the surgeon typically must work fast to unfold and properly position the prosthesis.

The elimination of stitching is beneficial in that it simplifies the surgery and saves time. However, in addition to the need to work quickly with such adhesive-based mesh prostheses, the additional layer of adhesive usually makes the overall mesh prosthesis stiffer, especially when it is dry, so that it cannot be rolled up into as small a diameter cylinder as non-adhesive based mesh products. It also makes the prosthesis thicker, further exacerbating the problem of minimizing its insertion profile in order to fit through the cannula of a trocar or an incision.

SUMMARY OF THE INVENTION

The present invention is an implantable self-adhering mesh prosthesis for reinforcing and/or repairing a defect in tissue that is easy to roll into a small diameter cylinder or other low-profile shape for passing through a trocar, incision, or other surgical instrument. More specifically, the adhesive may be applied to the mesh material in a pattern that leaves a significant portion of the surface area of the mesh prostheses material free of adhesive.

In one embodiment, the adhesive is applied only near the outer perimeter of the mesh prosthesis. In another embodiment, the adhesive is applied in spots over all or a portion of the surface of the mesh prosthesis. In yet another embodiment, the adhesive is applied in parallel lines on the surface of the mesh prosthesis and the mesh prosthesis may be rolled up around an axis parallel to the lines of adhesive.

DESCRIPTION OF THE PREFERRED EMBODIMENTS

Figure 1:
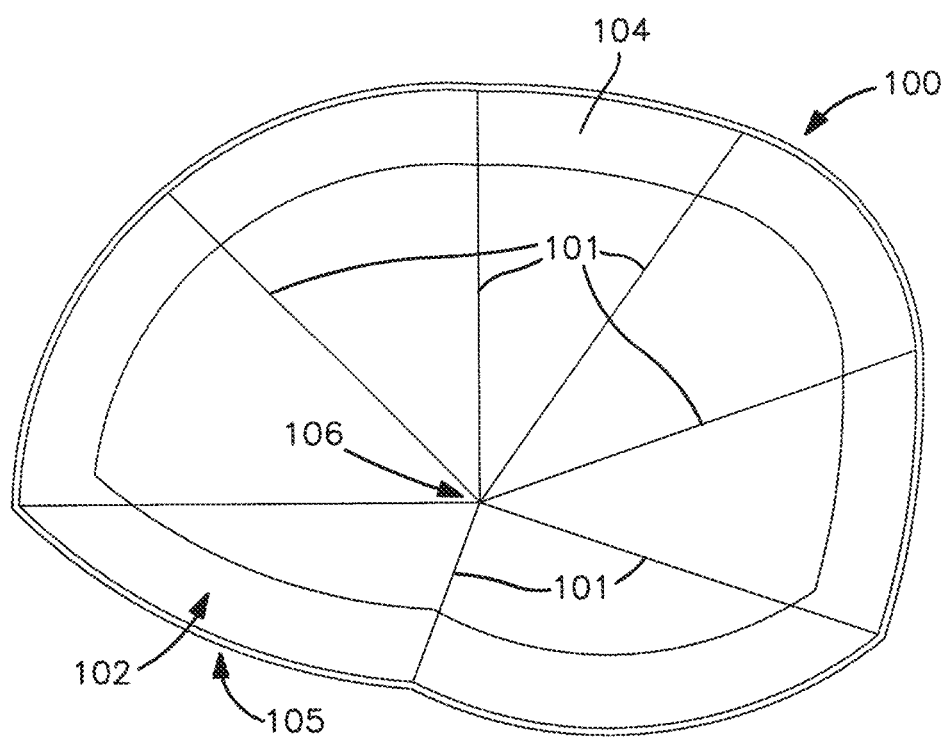
FIG. 1 is a plan view of a three dimensional mesh prosthesis for repairing tissue walls in accordance with the principles of a first embodiment of the invention.

FIG. 1 is a plan view of an exemplary self-adhering mesh prosthesis 100 for repairing an inguinal hernia. The prosthesis may, for example, be to any of the prostheses disclosed in any of U.S. Pat. Nos. 5,954,767; 6,368,541 and 6,723, 133, all of which are incorporated herein by reference in their entireties. For instance, prosthesis 100 may be a three dimensional prosthesis, as illustrated, or a flat mesh. The lines 101 emanating from near the center of the prosthesis correspond to creases in the fabric. Nevertheless, it is substantially sheet like, comprising two opposed major surfaces 104 (shown) and 105 (opposite surface 104 and not seen in FIG. 1). As used herein, the term "area" of the prosthesis refers to the geometric area of a major surface of the mesh prosthesis (either surface 104 or surface 105 as FIG. 1). Thus, the area of surface 104 is substantially the same as the area of surface 105, which, in turn, is substantially equal to the "area" of the prosthesis.

The band around the perimeter of surface 104 of prosthesis 100 is the adhesive 102. The majority of the surface 104 of the prosthesis 100 is free of adhesive. The adhesive-free majority of the surface 104, hence, is relatively more flexible than the perimeter portion of the surface that is covered in adhesive 102. It also is thinner. Thus, overall, most of the area of this prosthesis is less stiff than if the entire surface 104 were coated with an adhesive layer and, therefore, more easily rolled up into a small diameter cylinder or scrunched up into a small cross-section for passage through a passageway, such as the cannula of a trocar or an incision in the skin of the patient.

In many uses of self-adhering mesh prostheses, it is only, or at least substantially, the edge of the prosthesis that adheres the prosthesis to the tissue. Specifically, in inguinal hernia repairs, for instance, the area of tissue near the center of the mesh prosthesis, when it is in proper position at the implantation site, overlies the damaged or missing portion of the tissue wall. Accordingly, it is the adherence of the outer perimeter of the prosthesis to the still-healthy tissue that circumferentially surrounds the damaged or missing tissue that is most important.

An added benefit of applying adhesive only at the edges of the prosthesis 100 is that the adhesive may eliminate the need to heat seal the edges of the prosthesis. Particularly, it is common to heat seal the edges of a mesh prosthesis for at lest two distinct reasons. First, mesh prostheses commonly are formed of one or more layers of woven or knitted membranes of fibers of polypropylene and/or polyethylene (or other polymers). The ends of the polymer fibers at the edges of the prosthesis can fray if not heat sealed. Furthermore, heat sealing the edges of the prosthesis gives the edges an added stiffness or resilience that helps the prosthesis uncoil and expand to its original sheet-like shape upon exiting the trocar or other narrow opening in the relevant body cavity. Yet further, the coating can serve to "lock-in" the edges of the mesh/fiber to prevent snagging during delivery/deployment.

An edge band of adhesive can serve both of these functions, i.e., sealing the ends of the fibers to prevent fraying and, as already noted, making the edge of the prosthesis stiffer and, therefore, more resilient.

In use, a surgical grasper may be used to grasp the prosthesis at the intersection point 106 of the creases 101 and push the prosthesis through a restricted passageway, such as a trocar. The prosthesis 100 will scrunch up upon itself and around the jaws of the grasper with the adhesive-covered perimeter being the most trailing end of the folded prosthesis 100. It may be desirable to twirl the grasper around its longitudinal axis as it is pushed through the trocar to better cause the prosthesis 100 to fold up upon itself into the smallest diameter possible. Hence, the thickest and stiffest portion of the prosthesis, the part bearing the adhesive, is the last part to enter and pass through the opening, thus presenting a streamlined shape to pass through the trocar, incision, or other opening. However, note that, since the prosthesis 100 is not symmetrical about point 106, the band of adhesive 102 will be spread out somewhat in the longitudinal direction of the trocar when scrunched up and trailing behind leading point 106. Hence, the entire adhesive-bearing portion of the prosthesis (i.e., the portion that is likely to be the thickest and stiffest) will no be entirely longitudinally coextensive when the prosthesis passes through the trocar (or other passageway). Hence, in general, it will be desirable to grasp the prosthesis with the grasper that will lead the prosthesis through the passageway at a point that is not equidistant to all parts of the adhesive. In fact, it may be advisable to grasp the prosthesis 100 near its edge so that the adhesive band will be most spread out longitudinally when the prosthesis is scrunched up into a cylindrical profile for passing through the trocar or other passageway, thus permitting the prosthesis to be scrunched into the smallest diameter possible. For sake of clarity, the term longitudinal when applied to the passageway through which the prosthesis must pass generally means the direction in which the prosthesis moves through the passage. With regard to a trocar or any other instrument with a cannula, the longitudinal direction is understood fairly intuitively. However, it is perhaps not quite so intuitively understood when the passageway is an incision in the skin. Thus, the longitudinal direction generally refers to the direction transverse the opening through which the prosthesis is to pass.

Edge-adhesive embodiments such as illustrated in FIG. 1 may be best suited for procedures in which the prosthesis is passed through the opening as described above (i.e., in a somewhat haphazard scrunching, as opposed to being rolled into a specific, predetermined shape, such as a cylinder). In this embodiment, the opposing surface 105 does not bear any adhesive. This is a typical configuration for self-adhering mesh prostheses because they usually only need to adhere to tissue on one side thereof. However, embodiments of the invention in which both of the opposing major surfaces of the prosthesis bear adhesive are possible, such as for repairs in which it is desired to join together two adjacent and substantially parallel tissue walls or surfaces.

In embodiments that bear adhesive on both sides of the prosthesis, the adhesive on the opposing sides may be disposed in areas that are substantially opposed to each other. Thus, for instance, in a two-sided version of the FIG. 1 embodiment, the adhesive on the opposing side 105 may be disposed around the perimeter of the surface 105 (directly opposite the adhesive 102 on surface 104). Such embodiments can be configured to leave the majority of the area of the prosthesis adhesive-free, and, therefore, more flexible, whereas the areas bearing adhesive will be relatively stiffer because they bear two coats of adhesive.

In other embodiments, it may be desirable to avoid positioning the adhesive-bearing portions directly opposite each other. In such embodiments, a larger portion of the area of the prosthesis may bear adhesive (on one major surface or the other), but at least the areas of the prostheses that do bear adhesive (on one side or the other) may be less stiff than if those areas bore two layers of adhesive coextensively.

Figure 2:
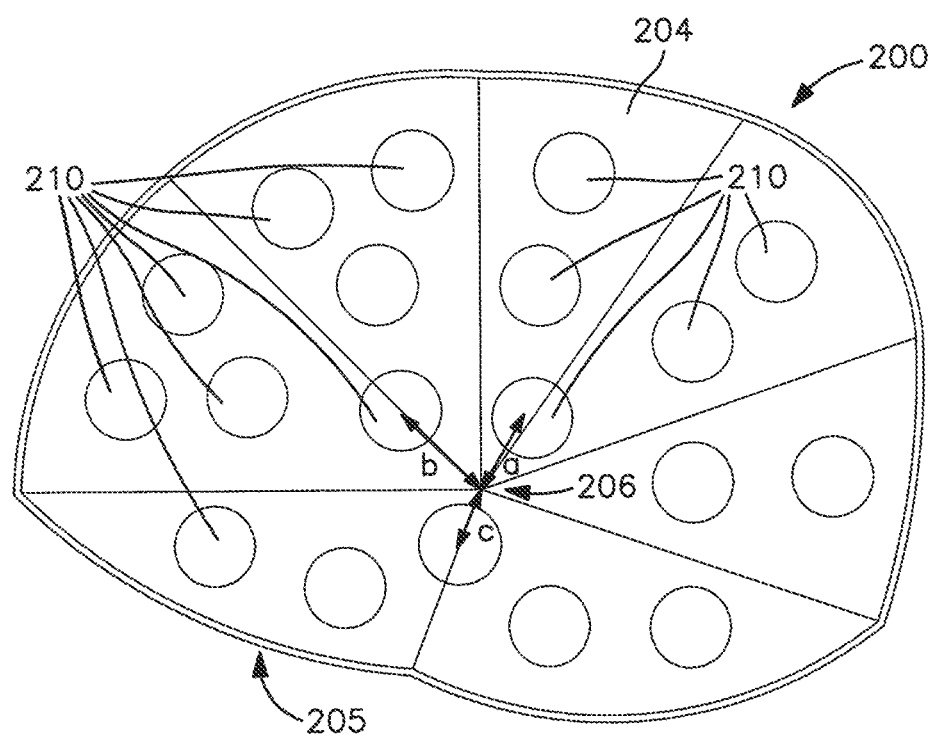
FIG. 2 is a plan view of a three dimensional mesh prosthesis for repairing tissue walls in accordance with the principles of a second embodiment of the invention.

FIG. 2 illustrates a second embodiment in which the adhesive is applied to the surface 204 or (surfaces 204, 205) of the prosthesis 200 in spots 210. In this embodiment, the entire area of the prosthesis 200 comprises interspersed areas of lower stiffness (i.e., areas where there is no adhesive) and higher stiffness (i.e., where there is adhesive 210). The spots of adhesive 210 may be distributed on the surface in a regular pattern or an irregular pattern. The spots of adhesive 210 may be laid out so that they are unlikely to overlap with each other when the prosthesis 200 is folded up for passage through the opening; that is, so that they minimally overlap with each other in the dimension transverse to the longitudinal axis of the trocar. Stated yet another way, the spots of adhesive 210 are spread out from each other maximally in the longitudinally direction of the trocar when the mesh is folded up on itself.

For instance, in one embodiment in which the prosthesis 200 is to be grasped by a grasper at point 206 and pushed through a trocar, the spots of adhesive 210 are distributed at different linear distances from point 206, e.g., distances a, b, c (between point 206 to the center of each different spot 210), in order to keep the spots 210 from being longitudinally coextensive with each other when the mesh is scrunched up inside the trocar trailing behind leading point 206.

Of course, the embodiment of FIG. 2 also may be rolled into a cylinder (like a cigar is rolled). If the prosthesis is intended to be rolled into a tube for passage through the relevant passageway instead of scrunched up behind a leading point, then the spots of adhesive 210 alternatively may be distributed on the surface 204 so as to minimize overlapping of the spots with each other when the prosthesis is rolled into a cylinder. Of course, there is nothing to preclude the possibility of selecting a single pattern for the spots that will minimize the relevant overlap of the spots with each other when the prosthesis is rolled into a cigar-like cylinder as well as when it is scrunched up behind a particular leading point, such as point 206.

The spots are shown as circular in FIG. 2. However, this is merely exemplary. The spots may be any shape, including, but not limited to, ovals, stars, and crosses.

Figure 3:
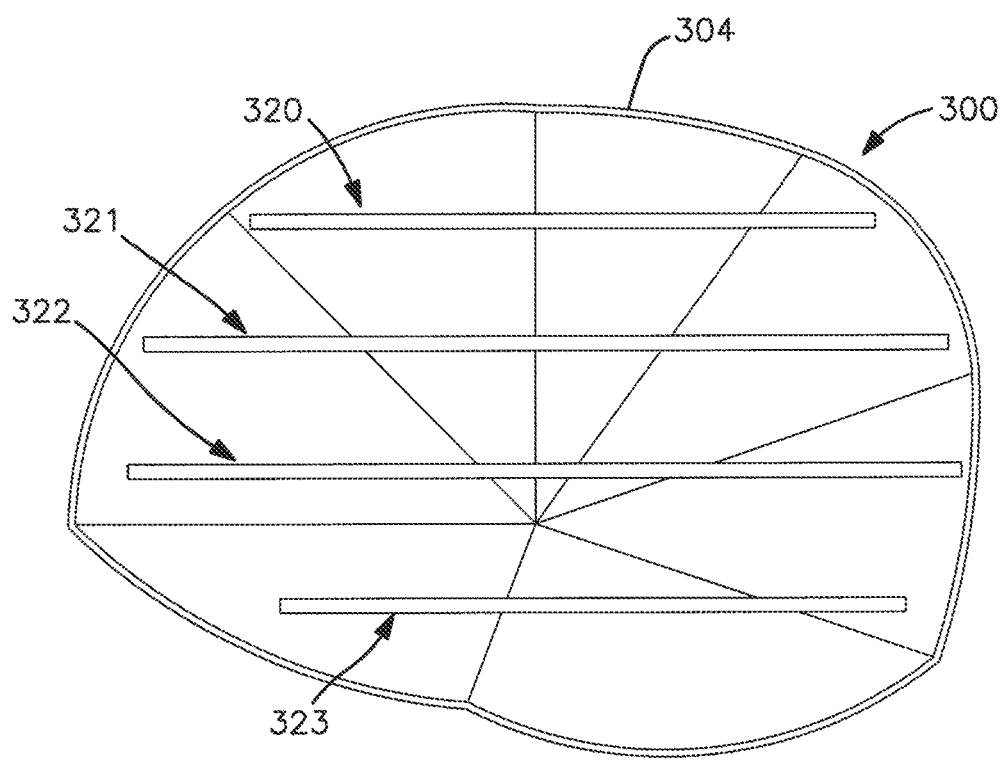
FIG. 3 is a plan view of a three dimensional mesh prosthesis for repairing tissue walls in accordance with the principles of a third embodiment of the invention.

FIG. 3 illustrates another embodiment, this one perhaps best suited to minimize the diameter of the prosthesis 300 when rolled into a cylinder. Particularly, in this embodiment, the adhesive is distributed in lines 320. 321. 322. 323. etc. on side 304. Preferably, the lines are parallel. In this embodiment, preferably, the prosthesis is rolled into a cylinder about a longitudinal axis substantially parallel to the adhesive lines 320. This axis will likely have the least resistance to rolling. The lines of adhesive 320 may be substantially continuous, as shown in FIG. 3. Alternately, as illustrated in FIG. 4, the lines may comprise intermittent line segments, such by line segment 420a, 420b, 420c, 421a, 421b, 421c, 422a, 422b, 422c, 423a, 423b, 423c, 424a, 424b, and 424c.

Figure 4:
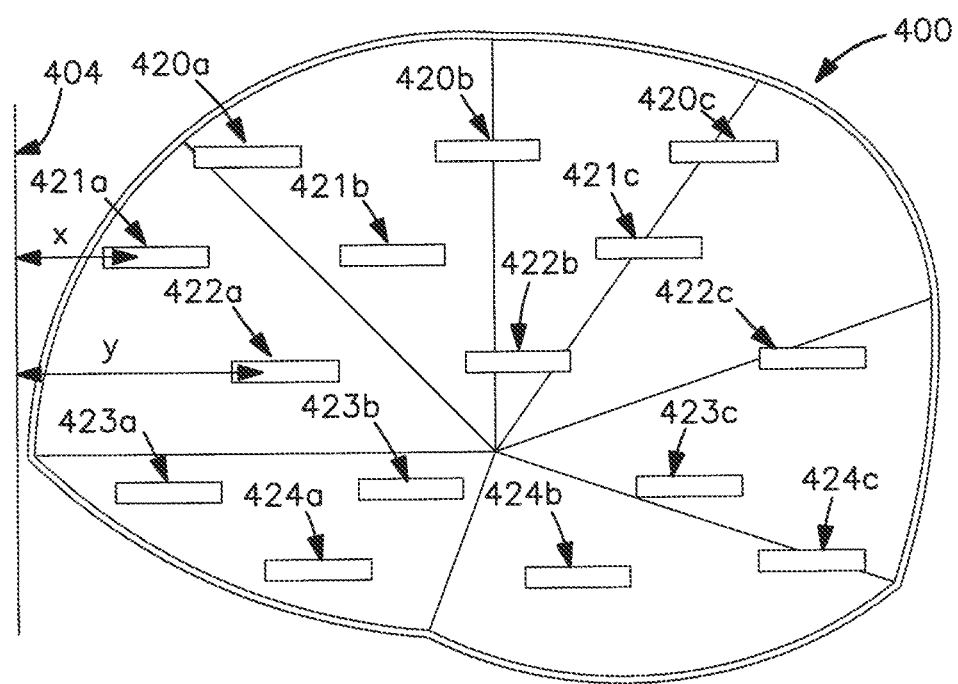
FIG. 4 is a plan view of a three dimensional mesh prosthesis for repairing tissue walls in accordance with the principles of a fourth embodiment of the invention.
Figure 5:
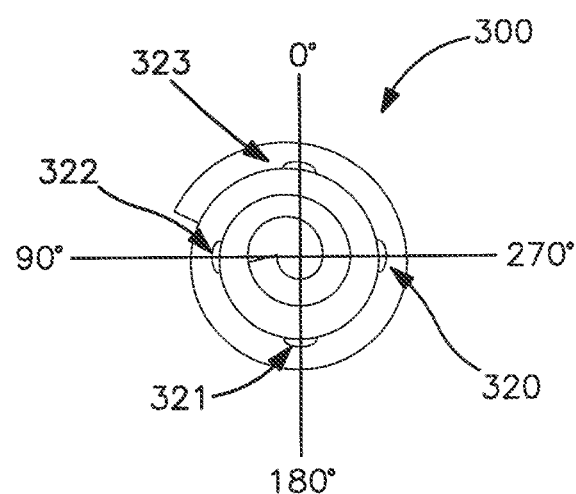
FIG. 5 is a longitudinal view of the mesh prosthesis of FIG. 3 rolled into a cylinder.

Again, the lines in either of the embodiments of FIG. 3 or FIG. 4 may be distributed evenly or unevenly so as to permit a minimum diameter when rolled up cigar-like into a tube. Particularly, a minimum diameter is probably achieved when the lines of adhesive do not radially overlap or at least minimally radially overlap with each other when the prosthesis is rolled up. FIG. 5 helps illustrate the concept of avoidance of radial overlap of the lines of adhesive. FIG. 5 shows the prosthesis 300 of FIG. 3 rolled up into a tube so that each adhesive line 320 is located at a different radial angle around the longitudinal axis of the rolled up prosthesis 300. For instance, as illustrated in FIG. 5, the four different lines 320 of adhesive are distributed at 0°, 90°, 180°, and 270° radially around the longitudinal axis of the rolled up prosthesis.

An alternate or additional way to minimize the diameter of the rolled up prosthesis is to utilize the intermittent line embodiment of FIG. 4 and linearly offset the portions of adhesive in the direction of the lines of adhesive so as to reduce or minimize longitudinal overlap of the adhesive-bearing portions when rolled up. For instance, note that the line segments 420a, 420b, 420c of adjacent lines 421 and 422 in the embodiment of FIG. 4 are longitudinally offset from each other as illustrated by reference distances x and y from transverse reference line 404.

Although described hereinabove in connection with adhesive, the invention is equally applicable to other forms of attachment, such as strips, spots, or edge bands of hook and loop type adhering mechanisms, such as Velcro™.

Having thus described a few particular embodiments of the invention, various alterations, modifications, and improvements will readily occur to those skilled in the art. Such alterations, modifications, and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed:

1. An implantable, self-adhering mesh prosthesis for repairing animal tissue comprising:

a sheet of mesh material comprising first and second opposing major surfaces, the sheet having a plurality of creases that intersect at an intersection point, the prosthesis configured with a three-dimensional shape when in an expanded self-supporting configuration of the prosthesis, the first major surface of the three-dimensional shape being asymmetrical and defining at an outer boundary a medial end, a lateral end, a first side between the medial end and the lateral end, and an opposed second side between the medial end and the lateral end, wherein a distance from the intersection point to the second side in a first side-to-second side direction is shorter than the distance from the intersection point to the first side in the first side-to-second side direction; and adhesive disposed on a first portion of at least the first major surface of the sheet, the first portion comprising less than a whole of the first major surface, the adhesive being disposed on the first portion prior to implantation of the mesh prosthesis to repair animal tissue, and the adhesive being disposed on the first major surface in a first segment and a second segment, where the first segment is located between the second side and the intersection point and the second segment is located between the first side and the intersection point, wherein a distance from one of the first segment and the second segment to the intersection point in the first side-to-second side direction is shorter than any distance from the other of the first segment and the second segment to the intersection point in the first side-to-second side direction, wherein the first segment and the second segment extend in the lateral end-to-medial end direction, and wherein an end of the first segment closer to the medial side is offset in the lateral end-to-medial end direction relative to an end of the second segment closer to the medial side.

2. The implantable, self-adhering mesh prosthesis for repairing animal tissue recited in claim 1, wherein each of the first segment and the second segment extend linearly.

3. The implantable, self-adhering mesh prosthesis for repairing animal tissue recited in claim 1, wherein each of the first segment and the second segment include a plurality of spaced bands of adhesive.

4. The implantable, self-adhering mesh prosthesis for repairing animal tissue recited in claim 3, wherein the plurality of bands in the first segment are offset in the lateral end-to-medial end direction relative to the plurality of bands of the second segment.

5. The implantable, self-adhering mesh prosthesis for repairing animal tissue recited in claim 1, further including a third segment of adhesive and a fourth segment of adhesive, wherein both the third segment of adhesive and the fourth segment of adhesive extend in the lateral end-to-medial end direction, both the third segment of adhesive and the fourth segment of adhesive are located between the first side and the intersection point, and the third segment is located between the fourth segment and the first segment in the first side-to-second side direction.

6. The implantable, self-adhering mesh prosthesis for repairing animal tissue recited in claim 5, wherein the sheet is rollable into a cylindrical tube so that none of the first segment, second segment, third segment, or fourth segment overlap each other.

7. The implantable, self-adhering mesh prosthesis for repairing animal tissue recited in claim 5, wherein each of the first segment, second segment, third segment, and fourth segment have a different distance from the intersection point when measured in the first side-to-second side direction.

* * * * *